United States Patent [19]

Van Hamont et al.

[11] Patent Number: 5,705,197
[45] Date of Patent: Jan. 6, 1998

[54] EXTRACTION PROCESS FOR PRODUCING PLGA MICROSPHERES

[75] Inventors: John Van Hamont, Ft. Meade, Md.; Curt Thies, Ballwin, Mo.; Robert H. Reid, Kensington; Charles E. McQueen, Olney, both of Md.; Jean A. Setterstrom, Alpharetta, Ga.

[73] Assignee: The United States of America as represented by the Secretary of the Army, Washington, D.C.

[21] Appl. No.: 698,896

[22] Filed: Aug. 16, 1996

Related U.S. Application Data

[63] Continuation-in-part of Ser. No. 242,960, May 16, 1994.
[51] Int. Cl.$^6$ ................................................ A61K 9/50
[52] U.S. Cl. ............................................ 424/501; 424/491
[58] Field of Search ...................................... 424/501, 491

*Primary Examiner*—Theodore J. Criares
*Attorney, Agent, or Firm*—Werten F. W. Bellamy

[57] ABSTRACT

A hybrid evaporation-extraction process for preparing microspheres of a poly(DL-lactide-to-glycolide) biodegradable polymer, comprising:

a. preparing a lyophilized biologically active material-sucrose matrix; adding acetonitrile solvent to biologically active material-sucrose matrix to form a solution;
  b. preparing a solution of a biodegradable poly (DL-lactide-co-glycolide) polymer by adding acetonitrile solvent to the polymer;
  c. adding the biodegradable poly (DL-lactide-co-glycolide) polymer acetonitrile solution to the biologically active material-sucrose acetonitrile solution;
  d. adding with stirring an oil containing lecithin to the poly (DL-lactide-co-glycolide) polymer-sucrose-biologically active material solution to evaporate acetonitrile and form an emulsion containing microspheres of poly (DL-lactide-co-glycolide) biodegradable polymers;
  e. adding the emulsion from step d. into a solvent selected from heptane, hexane, pentane or isopropanol; and
  f. collecting microspheres of poly (DL-lactide-co-glycolide) biodegradable polymers of from 1.0 to about 10.0 micrometers after filtration and washing with a fresh solvent selected from heptane, hexane, pentane or isopropanol.

10 Claims, 4 Drawing Sheets

F I G. 3
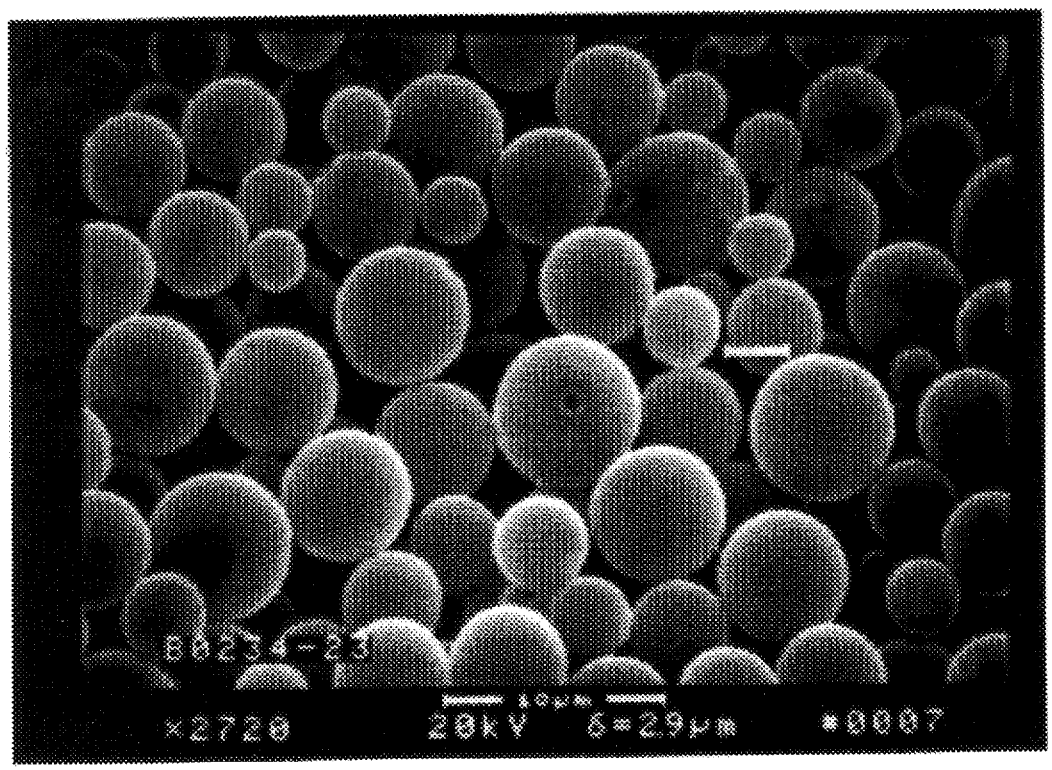

EXTRACTION PROCESS FOR PRODUCING PLGA MICROSPHERES

I. CROSS REFERENCE

This application is a continuation-in-part of U.S. patent application Ser. No. 08/242,960 filed May 16, 1994 pending.

II. GOVERNMENT INTEREST

The invention described herein may be manufactured, licensed and used by or for governmental purposes without the payment of any royalties to us thereon.

III. FIELD OF THE INVENTION

The invention relates to a hybrid organic solvent evaporation-extraction process for production of polylactide-co-glycolide microspheres for use in the delivery of vaccine antigens as well as other biologically active substances.

In this process, PLGA polymer is dissolved in a suitable solvent such as acetonitrile, whereupon a vaccine antigen or some other biologically active substance is blended either directly into the polymer solution or dispersed within lyophilized microparticles consisting of sucrose or other suitable stabilizer prior to being blended into the polymer solution. This polymer-core material mixture is then added to an oil phase such as mineral oil, silicone oil, or a synthetic oil and mixed vigorously under vaccum at predetermined temperature ranges from about 20° to 40° centigrade and stabilized by the addition of a suitable stabilizer such as lecithin. During this evaporative phase, an equilibrium developes wherein, on the one hand, micro globules of polymer-core material simultaneously are forming due to the mechanical action of the mixing and are sustained by the tendency of the oil external phase to isolate these globules from each other, and on the other hand, the nascent globules are re-coalescing together. The balance of this equilibrium is maintained by (1) the viscosity of the external oil phase which reduces that rate of re-coalescence as it is increased, and (2) the rate of evaporation of the acetonitrile which as it is increased, decreases the probability of two globules having the opportunity to re-coalesce by decreasing the length of time during which they are sufficiently solvated to undergo re-coalescence. The rate of solvent evaporation from the globules is a function of the solubility of the acetonitrile in the external oil phase at the temperature and pressure selected for the evaporative phase of the hybrid process.

During the second phase of this process, the residual acetonitrile and external oil phase are extracted from the nascent microspheres into a suitable solvent such as heptane, hexane, or pentane.

Control of the size range of microspheres produced by the hydrid process of the invention is achieved by selecting an emulsion oil in which the polymer solvent exhibits the appropriate solubility at the temperature and presssure of the evaporative phase. Greater solubility results in small spheres, while a lesser solubility results in larger diameter spheres.

IV. BACKGROUND OF THE INVENTION

Solvent Extract technology relies on the use of an organic solvent to remove the emulsion oil and the polymer solvent from the nascent spheres. However, to be successful, the polymer solvent must have a negligible solubility in the emulsion oil or else no emulsion would be formed during the emulsion process. Both the polymer solvent and the emulsion oil must be soluble in the extractant. As a result, this combination of soubilities required in the construction of an organic solvent extraction process usually results in a compromise in the function of one of more of the solvents employed. For example, the PLGA polymer is soluble in acetonitrile and because acetonitrile is somewhat polar, it exhibits negligible solubility in the emulsion oil. In order to extract the emulsion oil which is non-polar from the emulsion a non-polar solvent such as heptane is needed. However, solubility of the slightly polar acetonitrile is poor in this non-polar solvent. This necessitates the use of a large excess of heptane (4 liters per gram of microspheres manufactured) to be used in order to successfully extract the acetonitrile from the forming microspheres.

In the prior art, one successful method of microencapsulation is a solvent extraction process involving biodegradable lactide/glycolide copolymer (PLGA), acetonitrile (ACN), mineral oil and heptane. The PLGA is dissolved in ACN, and this solution is then added to mineral oil. Finally, heptane is used as a solvent to extract the ACN from the microspheres. While microspheres can successfully be prepared in this manner, the process is cumbersome. For example, the polymer/mineral oil emulsion is unstable, and must be transferred very quickly (within 3–4 minutes to the heptane for extraction). In addition, because of the low miscibility of ACN in heptane, the ratio of heptane to ACN used is on the order of 500 grams of heptane for every 1 gram of ACN. However, since heptane is a hazardous solvent, a ratio such as this is undesirable. Further, scale-up procedures are also complicated, since approximately 3 liters of heptane are required to produce just 1 gram of microspheres.

V. SUMMARY OF THE INVENTION

This invention provides biocompatible and biodegradable microspheres programmable for sustained delivery systems of vaccines, antibiotics, peptides, anesthetics, analgesics, and other biologically active substances.

The hybrid solvent evaporation-extraction process for producing PLGA microspheres of the invention reduces the otherwise prohibitive costs and risks associated with the use and minipulation of large quantities of organic solvents to far more managable levels and thereby makes the application of organic solvent-based PLGA microsphere technology far more economically attractive.

PLGA microspheres of the invention serve as biocompatible, biodegradable, non-toxic, programmable, controlled release delivery vehicles for a wide variety of pharmacologically active compounds such as vaccines, hormones, antibiotics, analgesics, anesthetics, interleukins and anticancer agents.

One objective of the invention is to provide PLGA microspheres as biocompatible, biodegrable, non-toxic, programmable, controlled release delivery vehicles for a wide variety of pharmacologically active compounds wherein, the micropheres effectively target their core materials because the size range of the microspheres are tailored to their intended us.

Another object of the invention is to provide a vaccine antigen deliverable into a phagocytic cell for processing and presentation to the immune system packaged into microspheres under 5 microns in diameter, as microsheres larger than 5µ will not be readily phagocytized.

A further object of the invention is to provide PLGA microspheres of a larger diameter size than 5 microns to serve as a depot for a drug or hormone, wherein the drug or hormone is releasable over a prolonged period.

A still further object of the invention is to provide PLGA microspheres as biocompatible, biodegradable, non-toxic, programmable, controlled release delivery vehicles for oral delivery of drugs to a depot within the intestinal mucosa, wherein the size distribution of the microspheres are tailored to that task.

In general, the invention is accomplished by utilizing a hybrid organic solvent evaporation-extract process for the production of PLGA polymers, wherein the PLGA polymer is dissolved in acetonitrile, whereupon vaccine antigen or some other biologically active substance is blended either directly into the polymer solution or dispersed within the lyopholized microparticles consisting of sucrose or other suitable stabilizer prior to being blended into the polymer solution.

This polymer-core material mixture is then added to an oil phase such as mineral oil, silicone oil or a synthetic oil and mixed vigorously under vacuum at a predetermined temperature ranging from approximately 20° to 40° C. and stabilized by the addition of a suitable stabilizer, such as lecithin.

During this evaporative phase, an equilibrium developes wherein, on the one hand, micro globules of polymer-core material simulataneously are forming due to the mechanical action of the mixing and is sustained by the tendency of the oil external phase to isolate these globules from each other, while on the other hand, the nascent globules are re-coalescing together.

The balance of this equilibrium is maintained by (1) the viscosity of the external oil phase which reduces the rate of recoalescence as it is increased, and (2) the rate of evaporation of the acetonitrile which as it is increased, decreases the probability of two globules having the opportunity to re-coalesce by decreasing the length of time during which they are sufficiently solvated to undergo re-coalescence. The rate of solvent evaporation from the globules is primarily a function of the solubility of the acetonitrile in the external oil phase at temperatures and pressures which have been selected for the evaporative phase of this hydrid process.

During the second phase of this hydrid organic solvent evaporation-extraction process, the residual acetonitrile and external oil phase are extracted from the nascent microsheres into a suitable solvent such as heptane, hexane, or pentane.

Control over the size range of microsheres produced by the hybrid process is achieved by selecting an emulsion oil in which the polymer solvent exhibits the appropriate solubility at the temperature and pressure of the evaporative phase. In general, greater solubility results in smaller spheres, while a lesser solubility results in larger diameter spheres.

The hybrid solvent evaporation-extract process of the invention results in up to a ten fold reduction in the volume of organic extractants required in the manufacture of PLGA microspheres. This can result in up to a 70% reduction in manufacturing cost associated with the production of PLGA microspheres for the controlled delivery of vaccines and other biologically active agents.

VI. BRIEF DESCRIPTION OF THE DRAWINGS

FIG. 3 shows PLGA microspheres approximately 10 millimicrons range, wherein aggregation is more a problem than when 0.25% w/v lecithin is used.

VII. DETAILED DESCRIPTION OF THE INVENTION

MATERIALS AND METHODS

Figure 1:
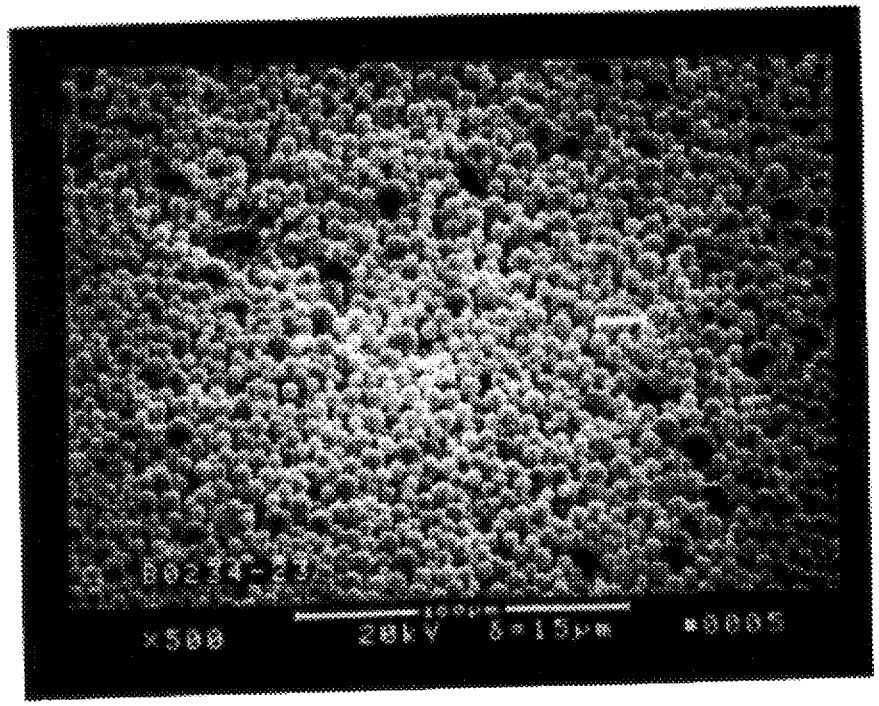
FIG. 1 Shows PLGA microspheres between 5–10 millimicrons, with very little aggregation.
Figure 2:
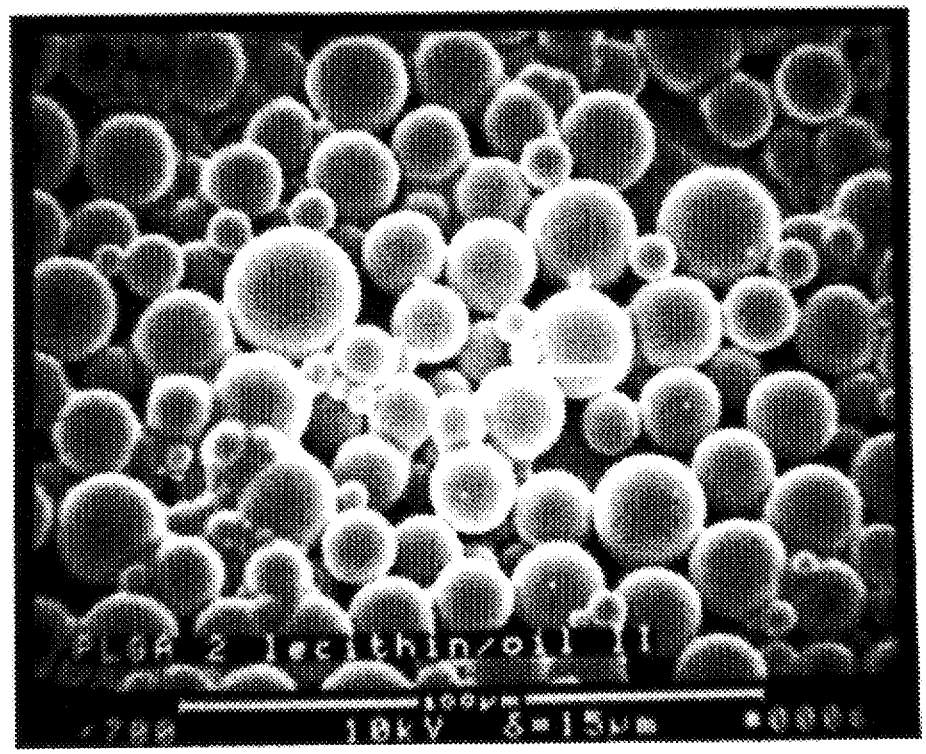
FIG. 2 shows PLGA microspheres between 5–10 millimicrons, with very little aggregation.

Five batches of vaccine placebo microspheres were produced with each of the four experimental emulsion oils. For each batch, one gram of High i.v. 50:50 DL (polylactide co-glyolide) was dissolved in 20 mls of dry acetonitrile. The polymer solution was then added to 75 mls of experimental emulsion oil containing 0.35 grams of lechitin and stirred at 500 rpm with a 1.5 inch impeller, under vacuum at either 20° C., 25° C., 30° C., 35° C. or 40° C. The length of these evaporative phases which ranged from 8 hours at 20° C. to 3 hours at 40° C. were adjusted to allow for similar net final evaporation of solvent for all batches. Following the evaporation phase of this process, the oil and residual acetonitrile were extracted from the nascent spheres by washing the spheres 3 times in a total of 400 grams of heptane.

Diameter and volume averages for each batch of spheres were determined by light microscopy and spread sheet analysis and analyzed as functions of oil weight, viscosity and evaporative phase temperature.

The emulsion oils used in this hybrid process included four different weights of machine oil (5W30, 10W30, 10W40, 15W50). Viscosities of each of these oils were determined at 20° C., 25° C., 30° C., 35° C. and 40° C. using a set of flow viscometers and expressed as centistokes.

In the instance where lecithin is used together with isopropanol to either eliminate or lessen the amount of heptane used in the method of microencapsulation, the microspheres are made by using a biodegradable 50/50 lactide/glycolide copolymer. 1 gram of copolymer is dissolved in 20 ml ACN for the encapsulation process. An oil soluble soya lecithin, Centrophase 31 is added to light mineral oil to obtain the desired concentration, preferrably, 0.25% w/v. The ACN-copolymer mixture is added to 75–150 ml of light mineral oil in a glass beaker (either 150 ml or 250 ml beaker depending on the amount of mineral oil) in a hood. The emulsion is stirred at 350–500 rpm for for 5–8 hours to facilitate the evaporation of ACN. A Janke Kunke IKA-WERK motor with a three bladed ship impeller is used to stir the mixture. Once most of the ACN has evaporated, stirring is stopped. ACN evaporation can be observed directly. When the ACN-copolymer mixture is first added to the mineral oil, beads of liquid are visible, and the beaker appears cloudy. As the ACN evaporates, the beads of liquid decrease in size, and the mixture becomes clear. When the liquid is clear, most of the ACN has evaporated. Evaporation of ACN can be verified by a weight loss experiment.

While Centrophase 31 is used, Lecigran 5750 may also be used as the lecithin component.

COLLECTION OF MICROSPHERES

Once ACN evaporation is complete, the stirring is stopped and the entire mixture is poured into a beaker of copolymer non-solvent and allowed to stir on a magnetic stir plate for several hours. The particles are then collected by filtration and allowed to air dry.

PARAMETERS EXAMINED

Several variables in the process were varied and their effects on particle size were evaluated. The variables studied include:

Polymer non solvent used;

Concentration of lecithin in mineral oil;

Volume of mineral oil necessary for emulsion;

Stirring speed;

Volume of isopropanol used to collect particles; and

Microsphere formation procedures.

CHARACTERIZATION

The main criteria for evaluating the microspheres are particle size and degree of aggregation. The desired particle size range is between 1 µm–10 µm. It is also desired to have free microspheres as opposed to aggregates of particles. Particle size was evaluated using a calibrated optical light microscope. Polaroid photographs were also taken of products from several experiments. Scanning electron photo micrographs of several samples were also taken.

Since the large heptane: ACN ratio necessary for extraction is due to the extremely low miscibility of ACN in heptane (0.002 g ACN/1 g heptane), the goal is to find a solvent in which ACN had a greater miscibility. Since ACN is infinitely miscible in isopropanol, isopropanol was chosen as a replacement for heptane. Mineral oil, however, is not infinitely miscible in isopropanol, therefore there are limits on how much mineral oil can be used. This depends on the concentration of surfactant in the mineral oil. The miscibility of the mineral oil (without lecithin) with isopropanol is approximately 0.26 ml mineral oil per 1 ml ispropanol.

Addition of an Emulsifier

The addition of an emulsifier to the mineral oil greatly stabilizes the PLGA/ACN emulsion in mineral oil, allowing the emulsion to be stirred for several hours before adding it to a solvent for extraction. Stirring of the emulsion for an extended period of time causes the evaporation of ACN from the system so less ACN will require extraction by the solvent. Two surfactants, Lecigran 5750 and Centrophase 31, were used. Lecigran 5750 is a solid powder, while Centrophase 31 is a viscous liquid. Although both surfactants gave identical results, Centrophase 31 is preferred because it dissolved more readily in the mineral oil.

Screening experiments showed that ACN evaporates from the microspheres fairly quickly; 5 ml ACN almost completely evaporates within 5 hours. With no ACN present after a matter of hours, limitations on the amount of solvent used are due only to the amount of mineral oil in the system and its miscibility with the solvent.

Concentration of Lecithin

Increasing the concentration of lecithin in mineral oil appears to decrease the miscibility of the oil with isopropanol. A series of experiments were carried out to determine the approximate miscibility of isopropanol and mineral oil with various concentrations of lecithin. 50 ml of isopropanol in a glass beaker was placed on a magnetic stir plate. Mineral oil was added dropwise, and the turbidity of the mixture was observed. As long as the mineral oil is still miscible with the isopropanol, the liquid will turn clear. Once no more mineral oil will dissolve in the isopropanol, the mixture remains cloudy.

It is therefore desirable to use as little lecithin as possible, so that the amount of isopropanol used will be minimal, also. The concentration (weight/volume %) of lecithin in the mineral oil was varied in several series of experiments. Favorable results were obtained with concentrations of 0.25% w/v or higher. When a concentration of 0.1% was used, the emulsion was not as stable and the particles often clumped together causing aggregation problems. A concentration of 0.2% w/v appeared successful at first, but also caused some particle aggregation (although not as much as 0.1%). The preferred concentration is 0.25% w/v, as this concentration gives consistent favorable results; however, as much as 0.35% w/v is operable in the context of the invention process.

Amount of ACN

Experiments indicated that the ACN used (5–10 ml) evaporated from the stirring mineral oil within several hours. Since the emulsion remains stable with the addition of an emulsifier, longer stirring times can be tolerated, so using more ACN in the process is an option. Dissolving 1 g of polymer in 5 ml of ACN produces a very viscous solution, and often causes aggregation problems. Several experiments were done using increased volumes of ACN to dissolve the polymer. Evaporation still occured within hours, and aggregation decreased. Successful results are obtained when 1 g of PLGA is dissolved in 20 ml of ACN (or 0.5 g dissolved in 10 ml ACN).

Volume of Mineral Oil Stirring Speed

A minimal volume of mineral oil is desirable, due to its limited miscibility with isopropanol. A series of experiments was carried out in which the amount of mineral oil used varied. Successful results were obtained by using as little as 75 ml of mineral oil (0.25% lecithin) for 1.0 g of PLGA in 20 ml ACN, at a stirring speed of 300 rpm. For 0.5 g of PLGA in 10 ml ACN, as little as 50 ml of mineral oil gave favorable results. However, the stirring speed had to be increased to 500 rpm. At 300 rpm, aggregation was a problem. Increasing the stirring speed decreased aggregation.

Volume of Isopropanol

The volume of isopropanol used to precipitate the PLGA particles depends on the concentration of lecithin in the mineral oil, and the volume of mineral oil used. As the concentration of lecithin in a fixed volume of mineral oil increases, the amount of isopropanol necessary to solidify the PLGA particles also increases. Increasing the volume of mineral oil used when the lecithin concentration is fixed increases the volume of isopropanol necessary. About 200 ml or less is necessary for 50 ml of mineral oil which is 0.25% lecithin (w/v).

A protocol using much less heptane (or isopropanol) was sucessfully developed. Although either isopropanol or heptane may successfully be used, isopropanol is more desirable since it is less flammable than heptane. A preferred recipe for PLGA microspheres prepared via solvent extraction is described below for preparing 1.0 g of PLGA microspheres of desired particle sizes.

Materials 1.0 g PLGA 20 ml ACN 50 ml light mineral oil (0.25% w/v lecithin)

200 ml isopropanol

Procedure

1) Add 20 ml ACN to 1.0 g PLGA in a 20 ml glass scintillation vial. Let polymer dissolve in ACN. This can be facilitated by occasional vortexing, and can take up to 30 minutes.

2) Prepare a mixture of 0.25% w/v lecithin in light mineral oil.

3) Pour 50 ml of the mineral oil in a 150 ml glass beaker, and place under a mixer which is set up in a hood. Place the 3-bladed ship impeller down into the oil about half way. Adjust the mixer to a stir rate of 500 rpm.

4) Pour the PLGA-ACN solution into the beaker of mineral oil stirring at 500 rpm. Avoid pouring the mixture down the side of the beaker.

5) Allow the mixture to stir for 5–8 hours at atmospheric pressure and room temperature. This will assure removal of most of the ACN by evaporation from the emulsion. This can be determined by observing the mixture as a function of agitation time. It will become progressively clearer as the ACN evaporates.

6) Once most of the ACN has evaporated, turn off the stirrer.

7) Place 200 ml isopropanol in a 1000 ml container. Place a magnetic stir bar in the isopropanol and put the container on a magnetic stir place.

8) Turn the stir plate on, and slowly pour the mixture from Step 5 into the isopropanol.

9) Let stir for 1 hour and turn off the stir plate.

10) Collect the microspheres via filtration and wash with fresh isopropanol. Let the particles air dry and then store in a tightly capped vial or centrifuge tube in a freezer.

Figure 4:
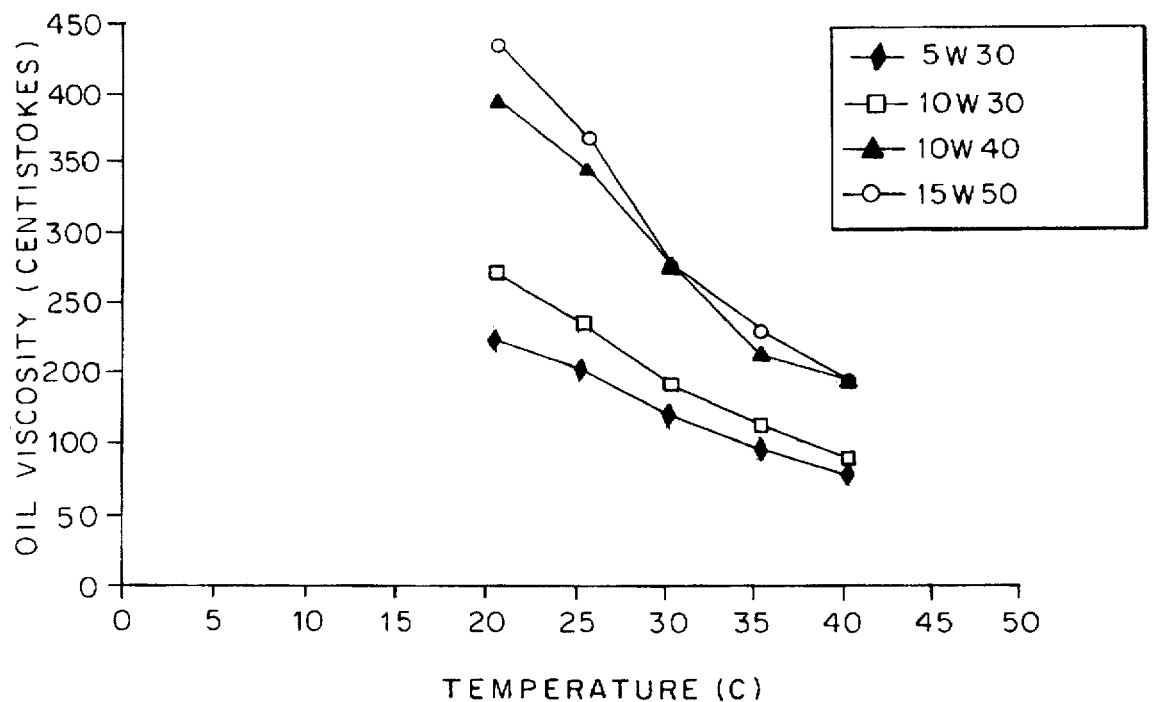
FIG. 4 shows the effect of temperature on viscosity of different machine oils.
Figure 5:
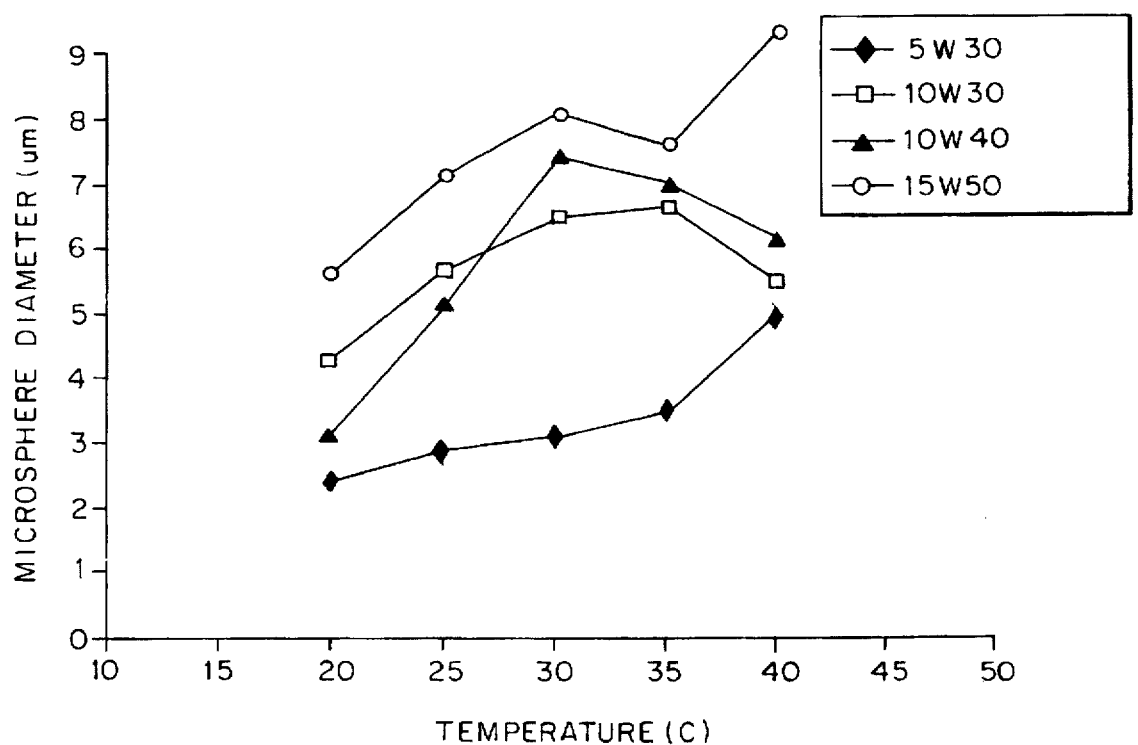
FIG. 5 shows the effect of emulsion temperature on sphere diameter for different machine oils.

When using a machine oil in replacement of mineral oil, the viscosity of each machine oil exhibited a linear decrease as the temperature was progressively increased from 20° C. to 40° C. (FIG. 4). Analysis of temperature versus viscosity revealed similar slopes for the 15W50 and 10W40 weight oils and also for the 5W30 and 10W30 weight oils (FIG. 4). Plots of emulsion temperature versus the resulting sphere volume averages revealed a predictable linear increase in the average sizes of microspheres as the temperature of each oil was increased from 20° C. to 30° C. during the evaporative phase of the process (FIG. 5). This linearity was lost as the evaporative temperature was increased from 30° C. to 40°. As the temperature was increased beyond 30° C., diameters decreased then increased with the 15W50 oil, increased with the 10W40 oil, increased then decreased with the 10W30 oil, and increased with the 5W30 oil.

Figure 6:
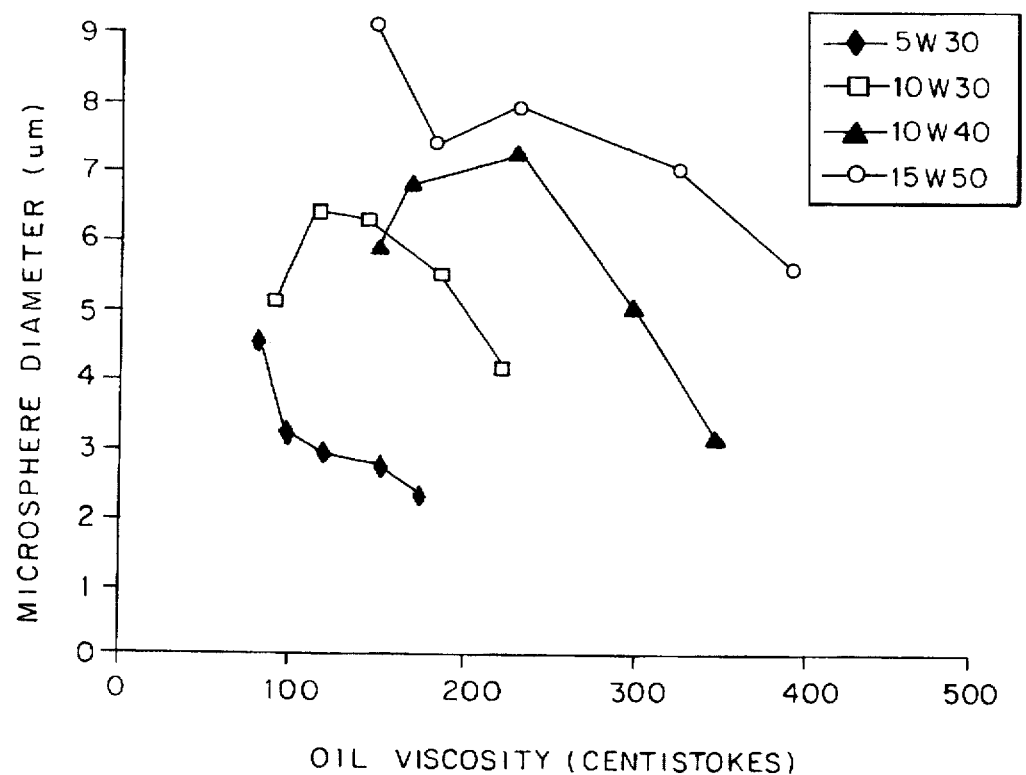
FIG. 6 shows the effect of oil viscosity on sphere diameter for different oils.
Figure 7:
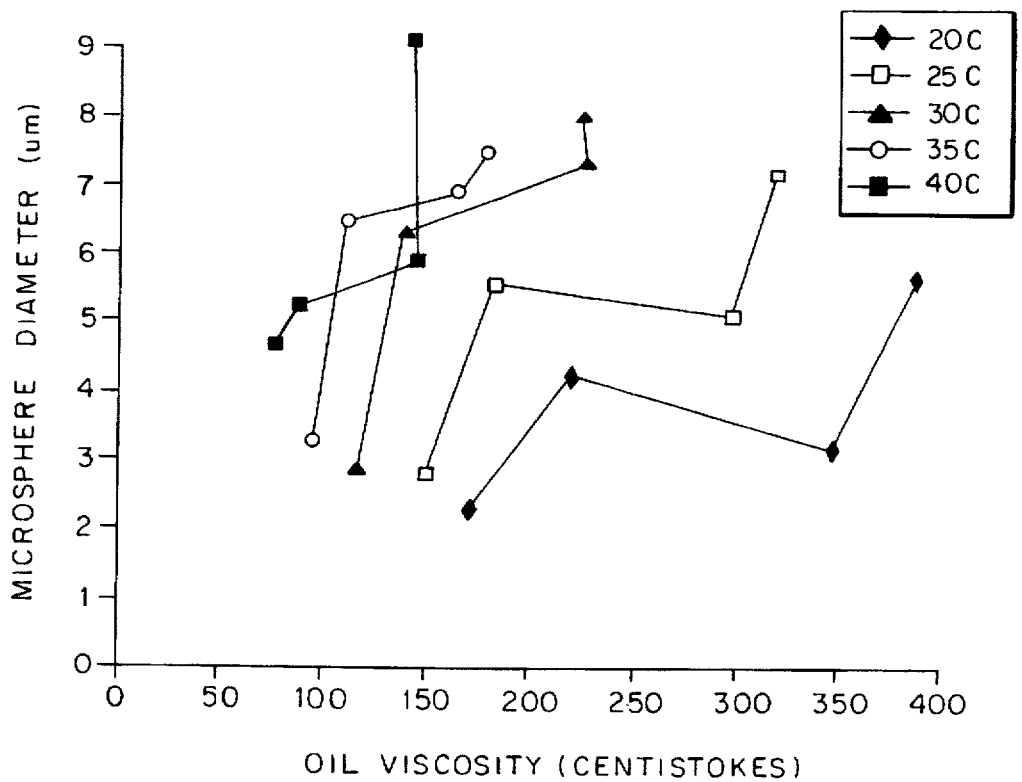
FIG. 7 shows the effect of oil viscosity on sphere diameter at different temperatures.

This lack of correlation between emulsion temperatures of over 30° C. and resulting sphere diameters continued to be evident when the viscosity of the oils at each temperature were compared against the resulting microsphere volume averages (FIG. 6). There was no correlation between emulsion viscosity and microsphere diameters at a constant temperature (FIG. 7). It therefore appears that the changes in performance of the test oils at temperatures above 30° C. are a function of the changes in the solubility of the acetonitrile in each oil as the temperature increases.

The microspheres diameters produced by our hybrid evaporation-extraction process can be predictably influenced by control of the temperature during the evaporative phase of the process provided that the temperature is kept below 30° C. The size ranges produced by this process are suitable for use in delivery of biologically active substances or vaccine antigens to the intestinal mucosa.

We claim:

1. A hybrid evaporation-extraction process for preparing microspheres of a poly(DL-lactide-to-glycolide) biodegradable polymer, comprising:

a. preparing a lyophilized biologically active material-sucrose matrix; adding acetonitrile solvent to biologically active material-sucrose matrix to form a solution;

b. preparing a solution of a biodegradable poly (DL-lactide-co-glycolide) polymer by adding acetonitrile solvent to the polymer;

c. adding the biodegradable poly (DL-lactide-co-glycolide) polymer acetonitrile solution to the biologically active material-sucrose acetonitrile solution;

d. adding with stirring an oil containing lecithin to the poly (DL-lactide-co-glycolide) polymer-sucrose-biologically active material solution to evaporate acetonitrile and form an emulsion containing microspheres of poly (DL-lactide-co-glycolide) biodegradable polymers;

e. adding the emulsion from step d. into a solvent selected from heptane, hexane, pentane or isopropanol; and f. collecting microspheres of poly (DL-lactide-co-glycolide) biodegradable polymers of from 1.0 to about 10.0 micrometers after filtration and washing with a fresh solvent selected from heptane, hexane, pentane or isopropanol.

2. The process of claim 1, wherein the oil is selected from machine oils of 5W30, 10W30, 10W40 and 15W50.

3. The process of claim 1, wherein the oil is mineral oil.

4. The process of claim 1, wherein the oil is a silcone oil.

5. The process of claim 1, wherein relative ratios between the lactide and glycolide are 50:50.

6. The process of claim 1, wherein said biologically active material is an antigen.

7. The process of claim 3, wherein said mineral oil is at a temperature from about 20° C. to about 40° C.

8. The process of claim 7, wherein lecithin is present in amounts of from about 0.1 to about 0.35% w/v of mineral oil.

9. The process of claim 8, wherein evaporation of acetonitrile is at a temperature less than 30° C.

10. The process of claim 9, wherein said stirring in step d. is about 500 rpm.

* * * * *